United States Patent [19]
Gupta et al.

[11] Patent Number: 4,989,225
[45] Date of Patent: Jan. 29, 1991

[54] CAT SCANNER WITH SIMULTANEOUS TRANSLATION AND ROTATION OF OBJECTS

[75] Inventors: Nand K. Gupta, Libertyville; John F. Moore, Lake Bluff, both of Ill.

[73] Assignee: Bio-Imaging Research, Inc., Ill.

[21] Appl. No.: 233,566

[22] Filed: Aug. 18, 1988

[51] Int. Cl.$^5$ ............................................. H05G 1/00
[52] U.S. Cl. ....................................... 378/10; 378/20; 378/58; 378/208
[58] Field of Search .................... 378/4, 10, 20, 57, 58, 378/208, 62; 73/622, 637; 209/589, 590

[56] References Cited

U.S. PATENT DOCUMENTS

| | | | |
|---|---|---|---|
| 2,179,859 | 11/1939 | Page | 378/57 |
| 3,384,235 | 5/1968 | Schulze et al. | 378/58 |
| 3,917,947 | 11/1975 | Fenton | 378/57 |
| 3,958,078 | 5/1976 | Fowler et al. | 378/57 |
| 4,368,641 | 1/1983 | McLeod, Jr. | 73/637 |
| 4,422,177 | 12/1983 | Mastronardi et al. | 378/10 |
| 4,710,946 | 12/1987 | Hinch et al. | 378/57 |
| 4,789,929 | 12/1988 | Nishimura et al. | 378/20 |
| 4,891,833 | 1/1990 | Bernardi | 378/146 |

*Primary Examiner*—Janice A. Howell
*Assistant Examiner*—David P. Porta
*Attorney, Agent, or Firm*—Laff, Whitesel, Conte & Saret

[57] ABSTRACT

A dynamic computed tomographic X-ray scanner concurrently translates and rotates an object as it passes through an X-ray field. This compound motion makes it unnecessary to perform sequential passes or to relocate X-ray equipment between passes to complete a scan. A conveyor may carry a series of closely spaced turntables to give greatly increased throughput; and coordinated translation and rotation, whereby all objects give comparable images, permitting the images to be compared to find defective products. Preferred geometries greatly simplify the image reconstruction mathematics, particularly where the X-ray source is at the center of a circular object path.

22 Claims, 4 Drawing Sheets

CAT SCANNER WITH SIMULTANEOUS TRANSLATION AND ROTATION OF OBJECTS

This invention relates to improved methods and apparatus for computed tomography.

Reference is made to copending patent applications Serial Nos. 122797, entitled "Automatic Dynamic Focusing For Computed Tomography" and 122909, entitled "Cam-Controlled Automatic Dynamic Focusing For Computed Tomography" filed on Nov. 19, 1987, assigned to the same assignee as the present application, for a further description of some of the elements disclosed herein.

The present invention is a fast and inexpensive computerized tomographic (CAT or CT) scanner particularly useful for nondestructively revealing the internal structure of industrial products.

This new CT scanner uses a penetrating radiation beam having a limited fan angle, but collects any desired angular distribution of views in a single pass of the object through the X-ray fan beam. The design retains the simplicity of 2nd generation CT scanners, and has a relatively narrow fan beam to facilitate reconstruction of good images.

According to the invention, a series of individual objects to be scanned, such as identical industrial parts, are mounted on a precision fixture. As it translates the mounted objects through an X-ray fan beam of angle phi, the fixture also simultaneously rotates each individual object. For example the objects may be translated through the fan beam in a straight line by a precision fixture carried by a conveyor belt. To obtain an angular distribution of view angles equal to theta, each object is rotated an angle lambda equals phi minus theta during its passage through the fan beam. The rotation may be about the longitudinal axis of the object to be scanned. The contributions to view angle distribution caused by various motions of the object are explained in detail in the Appendix at the end of the specification.

Alternatively, a carousel or other arcuate transport that carries each rotating object in an arc beta through the X-ray fan beam can be substituted for the linear conveyor belt. If the carousel translates each object through the fan beam of angle phi then, in order to obtain an angular distribution of view angles equal to theta, the rotation of each object should be lambda equals plus or minus the quantity phi minus theta minus beta.

This improved CT scanner has the following advantages:

1. A whole 180° or 360° scan can be accomplished within one traversal of the fan beam for most industrial objects.
2. If a series of objects separated from each other by a relatively small distance are on a single carousel or conveyor belt, each scan can be completed in a shorter period of time than in conventional 2nd generation CT scanners. In a conventional 2nd generation scanner, a significant amount of time is lost in collecting data through empty points in the fan beam where there is no object. The improved scanner minimizes the collection of data from empty points or "air."
3. For many industrial applications, a very large number of views is not essential. However, the views must be distributed over 180° to obtain a good image and to precisely locate flaws. This new method of CT scanning uses only a small number of detectors to collect a limited number of views, but these views can easily be spread over 180° without multiple passes of each object through the X-ray field.

The system described above is particularly useful for viewing high contrast objects, e.g. for determining the porosity of automotive pistons, measuring the dimensions of turbine blades, etc.

A preferred embodiment of the invention is shown in the attached drawings, in which.

Large, extensive and complex CAT scanners have to date mostly been used in medical rather than industrial applications. The invention is a simplified, less expensive, and faster CAT scanner for non-destructive examination of a series of identical mass-produced parts in an industrial environment.

The invention is proposed for use in detecting interior voids as small as 0.25 mm in castings, such as pistons. Presently available non-destructive testing methods other than CAT would not reveal such interior voids. Conventional CAT scanning techniques are slow and expensive and must be improved to provide a rapid and inexpensive industrial scanning method.

The first CAT scanners, which use a pencil X-ray beam and a single detector, are now called "first generation" machines. The pencil beam and the detector are translated together in a plane through the object to take a set of readings at a first angle. Then the pencil beam and detector are rotated to a new angle relative to the object in the same plane, and a new set of readings taken by translating them again in the plane relative to the object. For example, if the geometry is such that the detector covers a 1 degree arc, to take a set of readings covering 180 degrees of view requires 180 rotations of 1 degree each, with a set of translations for each angle setting.

The second generation of CAT scanners uses a fan-shaped X-ray beam that covers a range about 30–60 degrees and a plurality of X-ray detectors located in the plane of study. For example, the fan beam might cover 30 degrees and there might be a 30 degree array of adjacent 30 detectors, each covering 1 degree. If the object studied is larger than the fan beam width, the fan beam and detector are translated in the plane of study relative to the object to take one set of readings at a first angle relative to the object. Then the fan beam and its detector array are rotated in the plane of study relative to the object by 30 degrees, and a second set of readings are taken by translation of the fan beam and detector array relative to the object. This process of alternately indexing the angle and translating the object through the X-ray beam is repeated until sets of data covering 180 degrees of view have been taken. For a 30 degree fan beam, the angle between the fan beam and the object must be indexed by 30 degrees five times to take 180 degrees of view angles.

The reconstructed interior image of a CAT-scanned object sometimes has undesirable aberrations or distortions called "artifacts." Translation of the object studied relative to the array of detectors distributes the detected X-ray image data among the detectors in the array, tending to average out or reduce such artifacts.

If the object is smaller than the fan beam, some readings for a single angle can be quickly taken from the detector array without translating the fan beam relative to the object. However, it is still necessary to rotate the fan beam and its detector array relative to the object after a set of readings has been taken, in order to take sets of readings at other angles.

The readings are usually taken for either 180 degrees of view angles or 360 degrees of view angles. View angles of 180 degrees are sufficient when the object or the portion of the object being studied is small relative to the distance between the source of the X-ray fan beam and the detector. If the object being studied is large relative to this distance, undesirable distortions may appear in the reconstructed image. In such cases, readings are taken for a full 360 degrees of view angles to reconstruct a more accurate interior image of the object.

In contrast to the prior art method of alternately scanning and rotating, in the inventive scanning device each object translates through the fan beam concurrently with rotation of the object about an axis passing through its interior, such as its central axis. The object studied must be smaller than the width of the fan beam.

In the inventive CAT scanner, the object is rotated in a fan beam that typically has an angle of 30 to 60 degrees, though larger angles are also possible. If the object to be studied only needs a scan with 180 degrees of view angle, the angular width of the fan beam reduces the amount by which the object must be rotated. For example, if the fan beam and its detector array cover 30 degrees of arc, the relative rotation between object and fan beam (lambda plus beta) must be 150 degrees to accumulate data about 180 degrees of view angles. See the Appendix for a detailed explanation of the impact of the fan beam angle on view angle distribution.

When the X-ray fan beam is considerably wider than the width of the objects being studied, two or more objects may be irradiated side-by-side by the same fan beam at the same time. If two or more objects were located side-by-side in a prior art system which indexes the beam, there are certain angles of the beam that would send the same ray through more than one object before reaching the detector array. This would make reconstruction of the objects' individual images difficult. The present invention avoids such angles by virtue of the fact that, as the objects are translated through the fan beam, each is rotated about its own interior axis of rotation.

The rotation of an object need not be about a center axis, but the calculations for image reconstruction are simplified if the rotation is about a symmetrical interior axis of the object, such as a longitudinal axis of cylindrical symmetry. For many objects there will be some axis serving as a convenient center of rotation.

In one embodiment, the objects studied are continuously rotated while simultaneously being translated through a stationary fan beam that is always on. Measurements are taken by timing signals which latch the value of each detector in the detector array at fixed time intervals. The exposure needed to take a detector reading may be as short as a millisecond or as long as five seconds.

For applications where continuous motion would blur the image data, the translation and rotation are temporarily halted for detector readings. Then the object is again simultaneously translated and rotated until it reaches the position for the next detector readings.

Another approach is for the objects to be continuously translated through the path of the X-ray beam while being intermittently rotated. In the latter instance the X-ray beam could be turned off when the objects are rotating, and turned on only between increments of rotation.

Accordingly, the claims appended to this application refer to "concurrent" translation and rotation, by which terminology they comprehend any situation involving any rotation of the object which occurs during a traverse of the X-ray beam path, whether or not it is simultaneous with the translational motion and whether or not the beam is continuously on; as opposed to the prior art practice of rotating the object only between traverses of the beam path.

An embodiment relatively easy to construct translates the objects through the fan beam at a uniform velocity and simultaneously rotates the objects at a uniform rotational speed. It is less critical that the translation and rotation be exactly uniform than it is for the amount of translation and rotation between readings to be well determined for inclusion in the computations reconstructing the interior image. Therefore, a conveyor belt or other device for translating the objects is marked with position markings for detection by position encoders that read the markings. The encoder readings enable the computation device to confirm the exact position of each object for each reading. Similarly, the rotational devices have position markings detected by angular encoders whose output is fed to the computational device. The invention, however, includes embodiments where the translation or rotation are not uniform or not related to each other in a simple manner.

When the X-ray fan beam lies in a horizontal plane, each object may be rotated about a vertical axis of rotation while being translated by the conveyor belt or the like in a straight line in the horizontal plane.

If the horizontal translation is performed by a carousel, the carousel moves each object studied in an arc. The angle of the arc must be taken into account in determining the effective rotation of the object as it moves through the fan beam. The impact of object translation on the effective rotation of the object is shown in the Appendix.

After the various sets of data for different angles are collected from the detector array, a computer reconstructs the object's interior image from the data. Since an exact solution requires too much computation, the image is reconstructed by an approximation or estimate from the data. For example, a method of convolution back projection can be used to approximate the interior image.

To inspect a series of manufactured objects for defects, a reference or ideal set of data can be collected from an acceptable part. This is done in a learning or heuristic mode of the scanner by scanning acceptable parts and storing the detected data for later reference. Then afterwards when data is collected from the objects to be studied, it is compared with the ideal or reference data to discover any anomalies that might indicate defects.

Because mass-produced industrial objects are nearly identical to each other, the complete interior image need not be reconstructed to detect anomalies within the interior of a particular object. It is sufficient to compare the data from each object with pre-stored reference data from a known acceptable part. Even a limited number of measurements can be effective for such detection of anomalies, if the unknown object data was detected over a sufficient range of view angles. That is, the X-ray measurements should be taken over 180 degrees or 360 degrees of view angles, depending on the relationship between the size of the object studied and the distance between the X-ray fan beam source and the detector. In either case, the angle of the fan beam reduces the amount of rotation necessary to achieve the required range of views. For example, if the fan beam has an angle of 60 degrees and the views are to be distributed over 180 degrees, each object will only need to be rotated 120 degrees as it is translated through the fan beam. This effect is described in the appendix.

While the above description has referred to an X-ray beam, gamma rays produced by radio isotopes or other penetrating radiation could also be used as the radiation source. It is also possible to use ultrasound, electric potential, and optical beams (in the case of translucent or transparent systems). All of these, and any similar physical phenomena, are herein generically called "penetrating energy".

Figure 1:
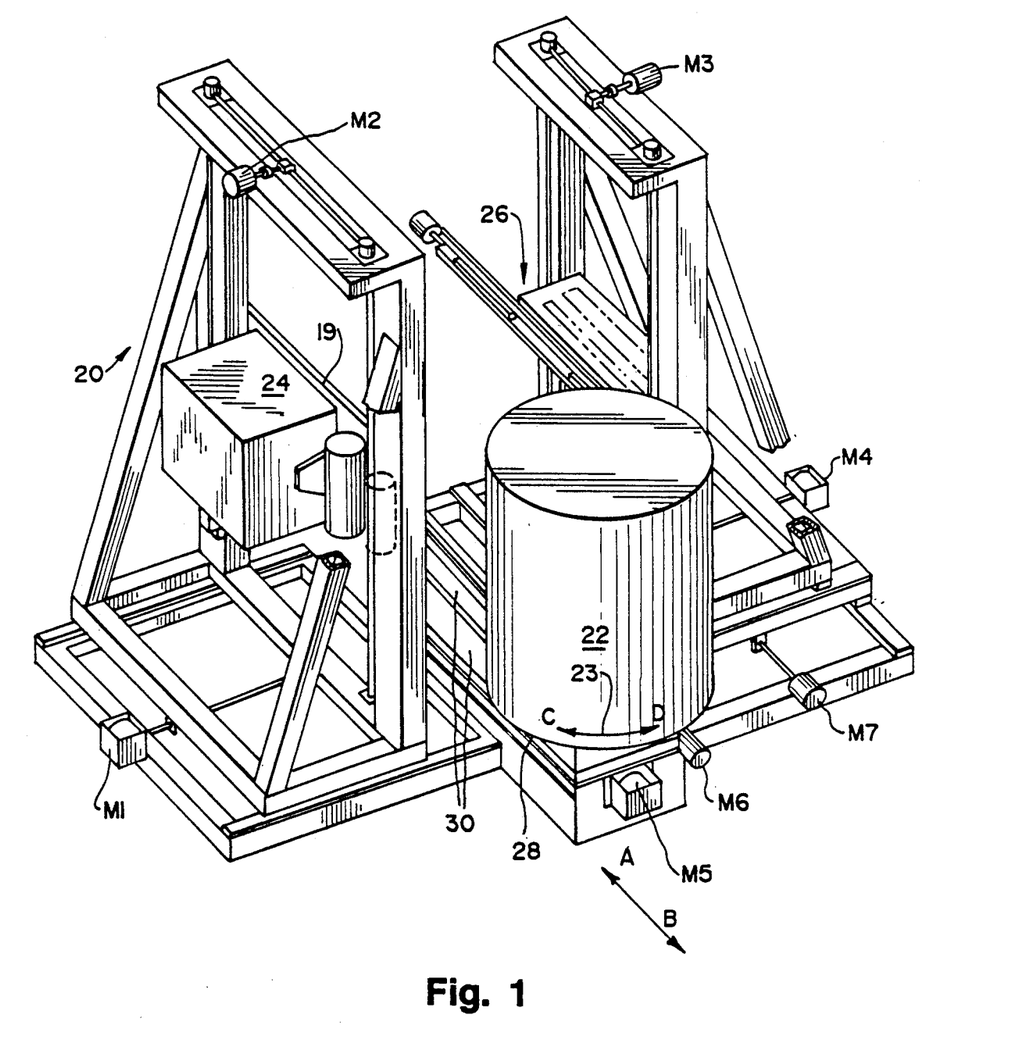
FIG. 1 is a perspective view which pictorially shows a CAT scanner incorporating the invention.

FIG. 1 pictorically indicates the inventive CAT scanner 20 as it is being used to X-ray an object 22 under study, which is here shown, by way of a generic example, as a simple cylinder. A frame 19 supports a source 24 of X-rays, such as a 150 KV or 420 KV tube, or a 2 MeV linear accelerator, and an opposed X-ray detector 26. The frame enables the X-ray source and the detector to move to any suitable points in a spaced parallel pair of vertical planes. The X-ray source 24 illuminates the detector 26.

The object 22 under test is mounted on a turntable 28 which rotates (arrow 23) as the object 22 is being X-rayed. The turntable 28 is mounted on a carriage which travels in direction A or B over track 30 concurrently with the rotation. Thus, the object 22 exposes all of its surfaces to X-rays as it travels with concurrent linear and rotary motion through the space between the source 24 and the detector 26. The object 22 is shown as rotating about its axis of cylindrical symmetry, which makes it easier to compute a tomographic image. However, with proper programming of a computer, the object may rotate about any axis.

The very same apparatus as in FIG. 1 has been used by the prior art in a different mode, in which the object 22 is rotated only *between* successive traverses of the X-ray beam path (see, for example, the above-cited co-pending patent applications); but the present invention represents the very first time that rotation has been employed *during the course of* a traverse of the beam.

While the tracks 30 provide a linear translation, it should be understood that other transport mechanisms could be used, such as a carousel which would provide a circular path.

A computer responds to the resulting signals from the detector 26 to construct a tomographic X-ray image of object 22. In one embodiment, the system is able to detect voids as small as 0.25 mm. A number of separate motors M1–M4 drive the supporting frame structure to position the X-ray source 24 and the detector 26 relative to the object 22 under study. A motor M5 operates a translational drive which moves the object 22 linearly (direction A or B). Motor M6 simultaneously moves the object rotationally (direction C or D). In many industrial tomographic systems only 180° of the surface of an object need to be scanned, so less than half a revolution would be required during traversal of the X-ray fan beam.

Figure 2:
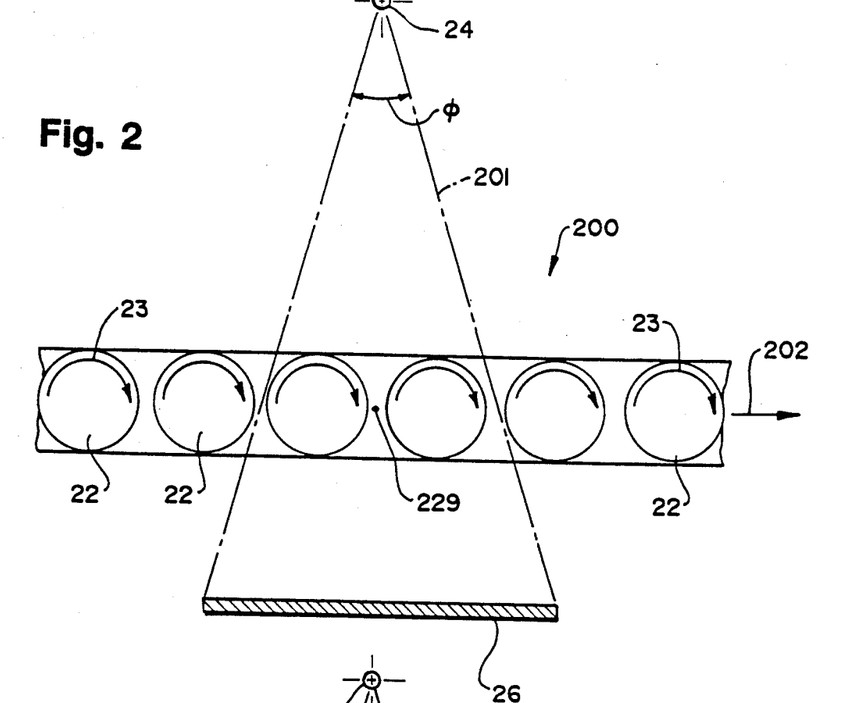
FIG. 2 schematically shows a series of objects being conveyed along a linear conveyor.
Figure 3:
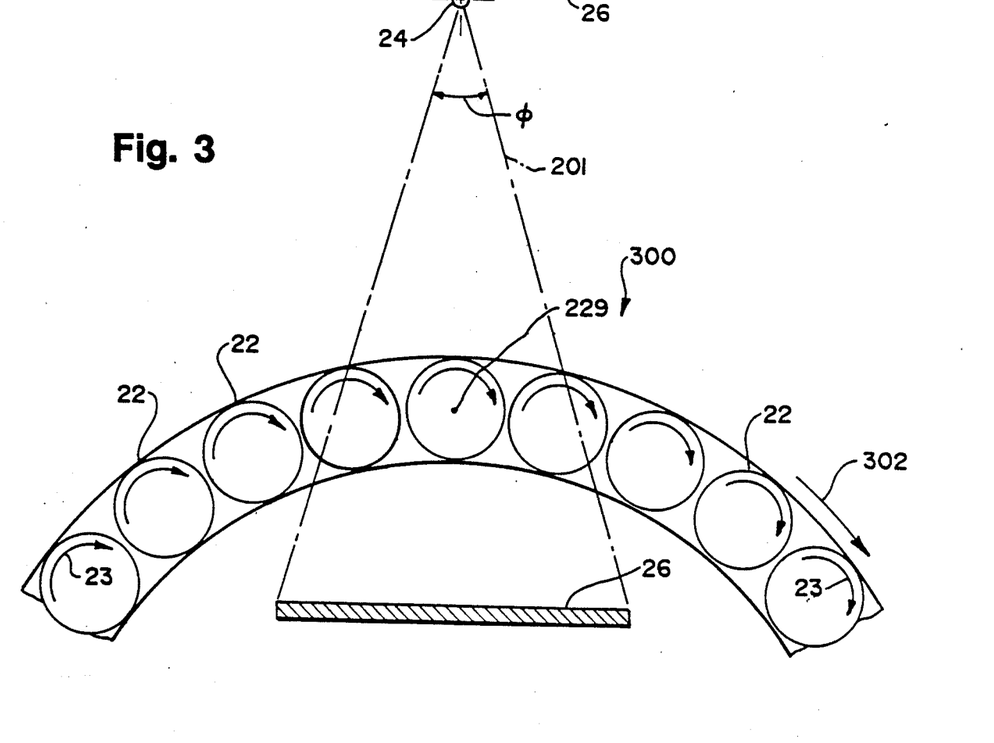
FIG. 3 schematically shows a series of objects being conveyed by a carousel.
Figure 4:
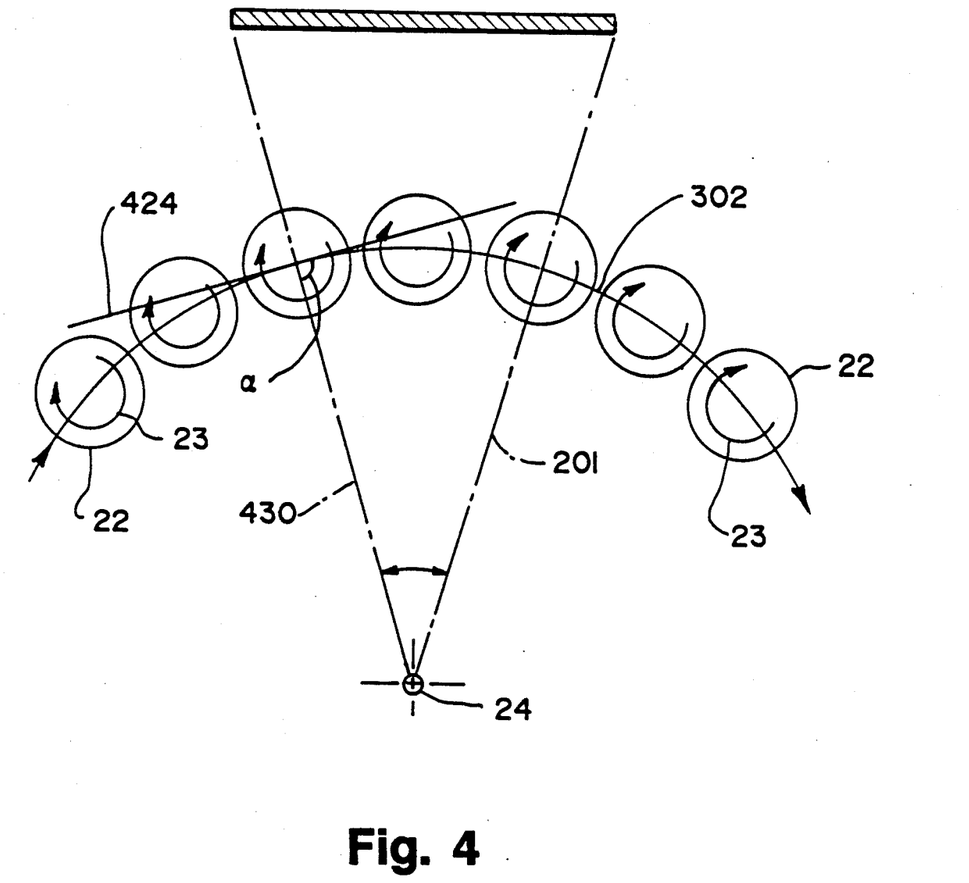
FIG. 4 shows an alternative wherein the X-ray source is at the center of a circle that defines the path followed by the moving object.

While FIG. 1 shows a single turntable 28, this is preferably only one of a series of turntables which closely follow each other along path 30. For example, FIGS. 2-4 show systems which are particularly attractive for industrial use in applications where a plurality of identical parts are to be nondestructively tested. In greater detail, either a linear conveyor 200 (FIG. 2) or a circular carousel 300 (FIGS. 3 and 4) is adapted to move a plurality of objects 22 successively along a straight path 202 or arcuate path 302 leading through an X-ray beam 201 produced by any suitable X-ray source 24 which is directed toward detectors 26. Each object is mounted on its own individual turntable 28 as in FIG. 1. The conveyor 200 or carousel 300 and the turntables 28 are geared or otherwise connected to move in synchronism, so that translation and rotation are simultaneous for each of the objects 22 while in the X-ray field.

If every object 22 traveling through the X-ray field experiences the same exposure, this simplifies the computations required to analyze the successive scans of the successive objects. It may be possible to detect flaws in the object simply by comparing successive images to detect differences therein. If every part is identical to every other part, any difference represents a defect of some kind in one of the parts. In some cases, it is also possible to program the computer to ignore some marginal defect. For example, if the inventive system detects voids as small as 0.25 mm, and if a void which is smaller than 0.50 mm is acceptable, the computer may be programmed to respond only when one image deviates more than 0.50 mm. from the previous image.

While the path of translation of the rotating objects may be straight as shown in FIGS. 1 and 2 or curved as shown in FIGS. 3 and 4, it should be noted that there is one particular configuration which has substantial advantages in reconstruction mathematics. This configuration places the object under study on a circular path with the X-ray source located at the center of the circle, as in FIG. 4.

This mathematical advantage results from the fact that, with the geometry of FIG. 4 the angle between the X-ray beam and an arbitrary reference point within any of the objects being examined is a function of only two independent variables: (a) the rate of rotation of the object being examined, and (b) the position of the object with respect to the center of the X-ray beam. That position can be thought of as the angle alpha (FIG. 4) between the local portion of the X-ray beam and the local tangent 424 to the path 302 of the objects 22 being examined.

When the motion of the objects 22 follows a straight line 202, as shown in FIG. 2, the angle alpha referred to at (b) above is equal to the inverse tangent of the ratio between: (c) the distance of the center of the object 22 from a point 229, which is its point of closest approach to the X-ray source 24; and (d) the distance from that point 229 to the X-ray source 24.

If, as in FIG. 3, the path 302 is circular and the X-ray source 24 is outside of the path 302, the mathematical function is considerably more complicated:

$$alpha = tan^{-1}(1 + [R \cos(X/R)]/L) - X/R$$

where alpha is the angle referred to above at (b), R is the radius of the circle of motion 302, L is the distance from the periphery of the circle 302 to the X-ray source 24, and X is the distance along the path 302 from the object 22 being examined to point 229.

However, in FIG. 4 where the X-ray source 24 is at the center of a circular path 302 over which the objects 22 move, the angle alpha referred to above at (b) is always 90°, since every radius 430 is at right angles to the corresponding tangent 424 of the circle 202. Accordingly, from the standpoint of image reconstruction mathematics, the geometry of FIG. 4 with the centrally located X-ray source 24 is the simplest of all, because it is not necessary to include the angle alpha as a variable.

An additional advantage of this geometry is that, in computer image reconstruction, it is often desirable to group the data in a manner which corresponds to equally spaced parallel beams within the object. Since data is taken at equal time intervals, an additional step which is often referred to as "interpolation" is required if the geometry does not yield a linear relationship between time and beam position. Only in the case of FIG. 4's central source 24 and concentric path 302 is this linear relationship obtained naturally. Where the motion of the object being examined is not concentric with the X-ray source, an additional computer step of interpolation is required. Therefore, for this additional reason it is simpler to practice the invention when the X-ray source is at the center of a circle traversed by the objects under study.

The next simplest geometry for image reconstruction is that of FIG. 2, because the inverse tangent function corresponding to the straight-line motion illustrated therein is substantially simpler to implement in a computer reconstruction than the complex formula given above for the geometry of FIG. 3.

The foregoing discussion, however, should not distract the reader from the generality of this invention. With suitable computer corrections, the invention in its broadest concept can be used when the objects being examined follow any straight, circular or arbitrarily shaped path, and when the X-ray source is located anywhere.

It will now be appreciated that the present invention provides apparatus and methods by means of which an entire 180° or 360 scan can be accomplished within one traversal of an X-ray beam. Each scan can be completed in a shorter period of time because no time is lost in collecting data through empty points in the fan beam where there is no object. The views are distributed over at least 180 to obtain a good image and to precisely locate flaws. The apparatus uses only a small number of detectors despite the elimination of multiple passes of each object through the X-ray field.

Moreover, a plurality of objects are able to follow each other in close succession through the X-ray beam, as compared to prior art procedures requiring multiple scans of each object to be entirely completed before the next object can enter the beam. This last feature greatly increases the throughput of a scanner, which can be economically important for high-volume industrial operations.

Those who are skilled in the art will readily perceive how to modify the invention. Therefore, the appended claims are to be construed to cover all equivalent structures which fall within the scope and spirit of the invention.

Appendix: View Angle Distributions

The angular range theta over which views of the scanned object are distributed is determined by the angular size of the X-ray fan beam phi, the amount of rotation lambda of the object while it is within the scope of the beam and, if the object follows a curved path, the amount of arc beta traversed by the object while within the scope of the beam.

This angular distribution of view angles is given by the equation theta equals phi minus beta minus lambda, observing a convention that clockwise angular displacements are considered positive.

It is helpful to examine the contribution to the range of view angles (theta) made by each parameter acting individually (with all other parameters remaining constant). It is most convenient to measure these contributions from the point of view of an observer on the object 0.

Define a reference ray X affixed to the object 0 to be scanned, and which runs through its center. Define a set Z composed of all rays extending from the source S through the center of object 0 for all possible positions of object 0 while illuminated by the source S. The reference ray R identifies that particular member of Z which runs through the center of object 0 in its current position. As 0 moves, R identifies different members of set Z. The total range of view angles theta may then be conveniently envisioned as the total relative displacement of the reference ray R with respect to the object's fixed reference ray X, or as the total angular segment of the object which is swept by the reference ray R solely as a result of the respective contributions of the individual parameters, as seen by an observer on the object.

Figure 5:
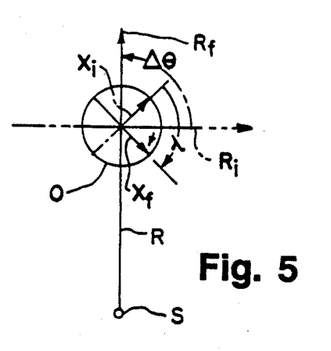
FIG. 5 shows the contribution to view angle distribution due solely to rotation of an object with respect to its transport.

The contribution due to rotation of the object with respect to the transport is the simplest to consider. In FIG. 5 is shown an object 0, an X-ray source S, and the source-to-object reference ray R. Index rays $X_i$ and $X_f$ identify a single fixed place on the object. The position of object 0 is shown both before rotation (indicated by $X_i$) and after rotation (indicated by $X_f$). The original position on the object of the source-to-object reference ray R before the object has rotated is labelled $R_i$. The final position of that ray is labelled $R_f$. The contribution to view angle distribution theta resulting from object rotation appears as delta theta and is measured by the angular displacement between the original position $R_i$ of the source-to-object reference ray, and the final position $R_f$ of that ray. If the object is rotated positively (clockwise) through an angle lambda, the source-to-object reference ray R appears to sweep in the negative (counter-clockwise) direction, resulting in a contribution to view angle distribution of negative lambda.

Figure 6:
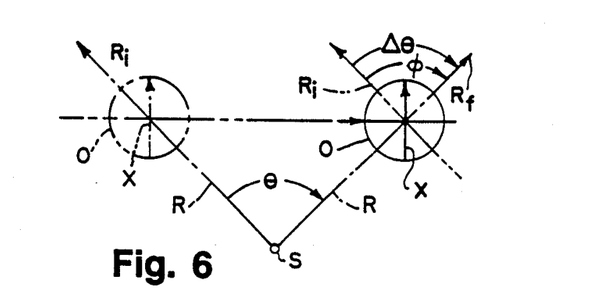
FIG. 6 shows the contribution to view angle distribution due solely to the size of the X-ray fan beam angle.

The contribution due to the size of the fan beam angle can be visualized most easily if the source beam is viewed, not as a fan beam, but rather as a thin beam which sweeps an angle equal to the angular breadth of the fan beam phi across the object, and is co-linear with the source-to-object ray R. This is shown in FIG. 6. The X-ray source appears as S. The index ray X identifies a fixed place on the object. Two views of the object 0 are shown representing the relationship of the object 0 to the source-to-object reference ray R as the X-ray beam sweeps an angle phi across the object. On the left side of FIG. 6, shown in broken lines, is the original position $R_i$ of the source-to-object reference ray before the beam sweep. On the right side of FIG. 6, in solid lines, is shown the final position $R_f$ of the source-to-object reference ray at the end of the sweep, with the original position $R_i$ superimposed. Thus, the contribution to view angle distribution theta resulting from the fan beam angle appears as delta theta and is measured by the angular displacement between the original position $R_i$ of the source-to-object reference ray, and the final position $R_f$ of that ray. As the source beam sweeps a positive (clockwise) angle phi across the object, the source-to-object measurement ray R sweeps with it. The resulting contribution to view angle distribution (delta theta) would thus be simply phi, and have a positive sign.

The contribution due to translation of the object depends on whether the object moves on a linear or curved path and, if curved, whether the center of path curvature is on the source side of the object or the opposite side of the object. The contribution due to the angular width of the beam (phi), realized through translation, has already been counted. Thus the angle of the source beam, as represented by the source-to-object reference ray R, must now remain constant. A convenient fiction, to aid visualization, is that the beam is generated from a planar source A rather than a point source B, resulting in parallel rays (as shown in FIG. 7) rather than divergent rays (as shown in FIG. 8).

If the object moves along a linear path, its translation does not independently contribute to the distribution of view angles. In FIG. 9, two views of the object 0 are shown representing the relationship of the object 0 to the source-to-object reference ray R as the object translates along a linear path T. The fictionally planar X-ray source is designated S. The index ray X identifies a fixed place on the object. On the left side of FIG. 9, in the broken lines, the object 0 is shown before translation, and on the right side of FIG. 9, in the solid lines, the object 0 is shown after translation. Since both the object orientation and source beam angle remain fixed, the source-to-object ray R does not sweep across the object. Thus, the contribution delta theta to view angle distribution theta as a result of the linear translation is zero.

If the transport moves in a curved path while maintaining the same face toward the center of curvature of the path, the transport necessarily revolves about its axis, turning the object along with it. This object rotation contributes to the view angle distribution independently of the previously considered object rotation modes. This contribution is shown in FIGS. 10 and 11.

Figures 7, 8, 9, 10, 11:
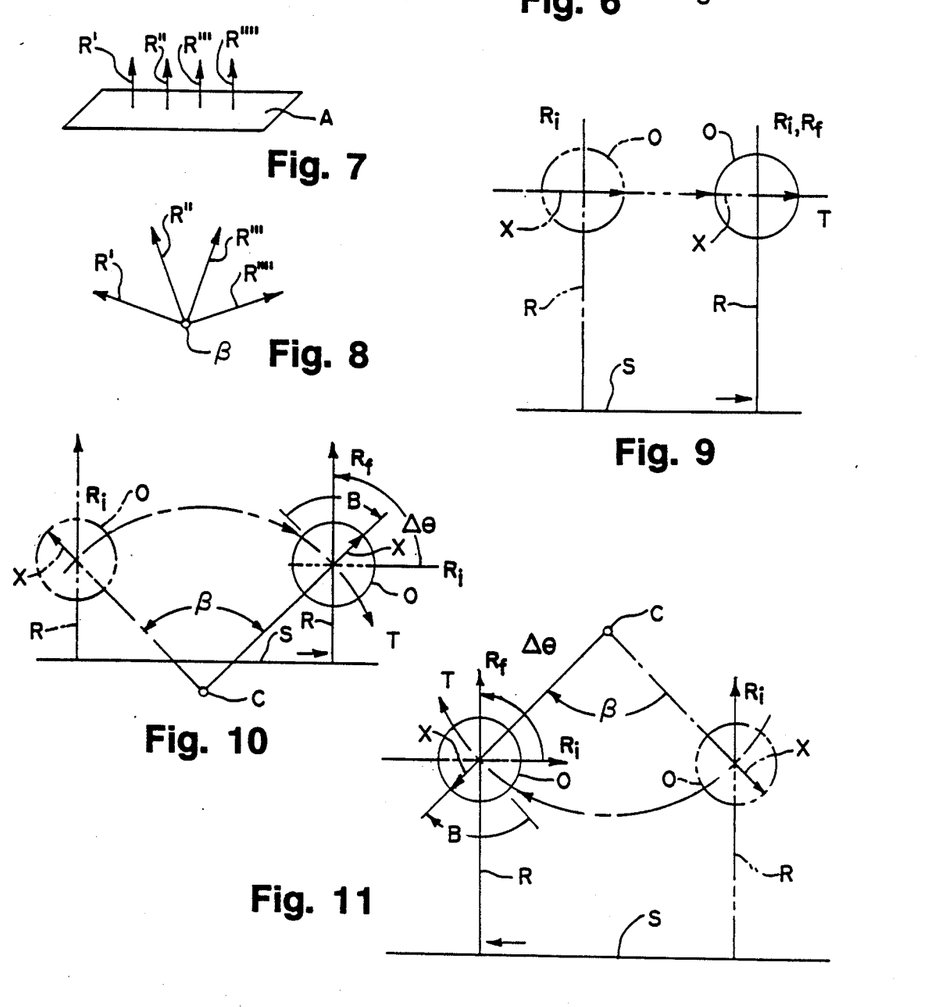
FIG. 7 depicts parallel rays emitted from a planar X-ray source.
FIG. 8 depicts divergent rays emitted from a point X-ray source.
FIG. 9 shows the contribution to view angle distribution due solely to object translation in a straight line.
FIG. 10 shows the contribution to view angle distribution due solely to object translation on an arcuate path the center of which is on the same side of the object as the source.
FIG. 11 shows the contribution to view angle distribution due solely to object translation on an arcuate path the center of which is on the opposite side of the object from the source.

Assume the center C of the circular path T is on the same side of the object as the X-ray source S as shown in FIG. 10. Two views of object 0 are shown representing the relationship of the object 0 to the source-to-object reference ray R as the object translates along a circular path T. The fictionally planar X-ray source appears as S. The index ray X identifies a fixed place on the object. The rotation of the circular transport appears as beta. The left side of FIG. 10, in broken lines, shows the original position $R_i$ of the source-to-object reference ray before translation of the object along the curved path by the transport. FIG. 10, in solid lines, shows the final position $R_f$ of the source-to-object reference ray at the end of the translation, with the original position $R_i$ superimposed. Thus, the contribution to view angle distribution theta as a result of the rotation of the transport appears as delta theta and is measured by the difference between the original position $R_i$ of the source-to-object reference ray, and the final position $R_f$ of that ray. A clockwise (positive) arc beta of the transport causes an equivalent rotation of plus beta by the object. With respect to the object, the source-to-object reference ray R sweeps in the counter-clockwise (negative) direction, resulting in a contribution to view angle distribution of negative beta.

Suppose the center of the curved transport is on the opposite side of the object as the source, as shown in FIG. 11. Again, two views of object 0 are shown representing the relationship of the object 0 to the source-to-object reference ray R as the object translates along a curved path T. The fictionally planar X-ray source appears as S. The index ray X identifies a fixed place on the object. The rotation of the circular transport appears as beta. On the right side of FIG. 11 is shown the original position $R_i$ of the source-to-object reference ray before translation of the object along the curved path by the transport. On the left side of FIG. 11 is shown the final position $R_f$ of the source-to-object reference ray at the end of the translation, with the original position $R_i$ superimposed. Thus, the contribution to view angle distribution theta as a result of the rotation of the transport appears as delta theta and is measured by the difference between the original position $R_i$ of the source-to-object reference ray, and the final position $R_f$ of that ray. A clockwise (positive) arc beta of the transport causes an equivalent rotation of plus beta by the object. With respect to the object, the source-to-object reference ray R sweeps in the counter-clockwise (negative) direction, resulting in a contribution to view angle distribution of negative beta.

We claim:

1. A computed tomography scanner comprising a source of penetrating energy, detector means positioned to receive said rays from said source, means for translating an object along a translation path to interpose said object between said source and said detector, computer means responsive to said detector for constructing a tomographic image of said object, said means for rotating said object concurrently with said translation.

2. A computed tomography scanner comprising a source of penetrating energy, detector means positioned to receive said rays from said source, means for translating an object along a translation path to interpose said object between said source and said detector, computer means responsive to said detector for constructing a tomographic image of said object, and means for rotating said object concurrently with said translation, said object rotation occurring about an axis non-parallel to said translation path.

3. The scanner of claim 1 or 2, and a turntable for providing said rotating motion mounted on a conveyor for providing said translating motion.

4. The scanner of claim 3, and means for separately driving said turntable and said conveyor for independently providing said translation and said rotation.

5. The scanner of claim 3, wherein said conveyor is an arcuate transport which moves said objects over an arcuate path.

6. The scanner of claim 5, wherein said source of penetrating energy is located at the center of said arcuate path.

7. The scanner of claim 1 or 2 wherein said translating means is so arranged that there is a constant angle between a tangent to said path and a straight line extending between said object and said source of penetrating energy.

8. The scanner of claim 1 or 2 wherein said source of penetrating energy provides a fan-shaped beam pattern for bathing said object with penetrating energy as it concurrently rotates and translates.

9. The scanner of claim 1 or 2 wherein said object rotates about an axis of symmetry.

10. The scanner of claim 1 or 2 wherein said object rotates about an axis which is not an axis of symmetry, and said computer means is programmed to compensate for said asymmetry.

11. The scanner of claim 1 or 2 wherein said path is linear.

12. The scanner of claim 1 or 2 wherein said path is arcuate.

13. The scanner of claim 12 wherein said path is circular.

14. The scanner of claim 13 wherein said source of penetrating energy is at the center of said circular path.

15. The scanner of claim 8 wherein said translating and rotating means are arranged so that a plurality of said objects follow each other along said path sufficiently closely to be simultaneously bated by said fan-shaped beam pattern.

16. A computed tomography penetrating energy scanner comprising means for conveying a plurality of objects through a penetrating energy beam in sufficiently close succession that at least two of said objects are within said penetrating energy beam for at least some positions of said conveyor, means associated with said conveying means for rotating said objects while they are in said penetrating energy beam, means for gathering penetrating energy images of said objects while they are within said penetrating energy beam, and means responsive to said penetrating energy images for computing an internal image of said objects.

17. The scanner of claim 16 wherein said conveying means is a linear conveyor and said rotating means are turntables mounted on said conveyor.

18. The scanner of claim 16 wherein said conveying means is an arcuate transport and said rotating means are turntables mounted thereon.

19. The scanner of claim 18, wherein said arcuate transport is a circular carousel, and means for generating said penetrating energy beam is located at the center of motion of said carousel.

20. The scanner of claim 16 wherein said conveying means conveys said object over a path such that there is a constant angle between a tangent to said path and a straight line extending between said object and said source of penetrating energy.

21. The scanner of claim 1, 16 or 2 in which said rotation is at least 180°.

22. The scanner of claim 1, 16 or 2 in which said rotation is 360°.

* * * * *